United States Patent [19]

Croom, Jr. et al.

[11] Patent Number: 4,647,567

[45] Date of Patent: Mar. 3, 1987

[54] METHOD OF RELEASING GROWTH HORMONES

[75] Inventors: Warren J. Croom, Jr., Cary; Winston M. Hagler, Jr., Raleigh, both of N.C.

[73] Assignee: North Carolina State University, Raleigh, N.C.

[21] Appl. No.: 635,904

[22] Filed: Jul. 30, 1984

Related U.S. Application Data

[63] Continuation-in-part of Ser. No. 596,929, Apr. 5, 1984.

[51] Int. Cl.4 .............................................. A61K 31/44
[52] U.S. Cl. ................................................... 514/299
[58] Field of Search ........................................ 514/299

[56] References Cited

PUBLICATIONS

News and Comment from the Institute of Biology and Medicine, Michigan State University, vol. 4, No. 4, (Apr. 1968), "New Drug Stimulates Exocrine Glands; Might Help Cystic Fibrosis Patients".

Biochemical Pharmacology, vol. 19, pp. 424–433, Aust.

Primary Examiner—Frederick E. Waddell
Attorney, Agent, or Firm—Bell, Seltzer, Park & Gibson

[57] ABSTRACT

A method of promoting the release of growth hormones in an animal comprised of administering a low level dosage of slaframine or a chemical compound which releases the 1-keto-6-aminooctahydroindolizine.

8 Claims, No Drawings

METHOD OF RELEASING GROWTH HORMONES

This application is a continuation-in-part of our pending application Ser. No. 596,929 filed Apr. 5, 1984 the specification and disclosure of which are incorporated herein by reference.

FIELD OF THE INVENTION

This invention relates to the use of purified slaframine, its precursors, derivatives, salts and metabolites, to release growth hormones in fowl and other animals, including humans, in a controlled manner, so as to facilitate the production of larger and less fatty species and treat certain hormonal disorders such as those related to dwarfism.

BACKGROUND OF THE INVENTION

Our pending application Ser. No. 596,929 relates to a method for altering various digestive parameters using parasympathomimetic compounds. Recently, we have discovered that one such compound, purified slaframine (1-acetoxy-6-aminooctahydroindolizine), its derivatives, salts and metabolites promote the release of growth hormones in animals. Furthermore, we have discovered that slaframine, its salts, derivatives and metabolites achieve this effect in a controlled manner, at relatively low level dosages and without debilitating side effects.

SUMMARY OF THE INVENTION

A primary object of this invention is to provide a method, for controllably releasing growth hormones in animals without debilitating side effects.

Another object of this invention is to provide a method for producing larger and heavier livestock.

Another object of this invention is to provide a practical method for beneficially altering the process of assimilation of food by young animals so that a lesser proportion of foodstuffs become body fat and so that the relative proportion of body fat to muscle is reduced.

Still another object of this invention is to provide a method for treatment of certain forms of dwarfism.

Administration to animals of low level doses of slaframine, its precursors, salts, derivatives and metabolites promotes the release of growth hormone, facilitating achievement of the foregoing objects. Moreover, in addition to their effects upon fowl, cattle and other livestock, low level dosages of slaframine are believed to be useful, in accord with this invention, in treating certain human disorders, including certain forms of dwarfism.

When slaframine is activated in the body, it forms 1-keto-6-aminooctahydroindolizine, which is believed to be the active metabolite for purposes of this invention and which is depicted in FIG. 1, below:

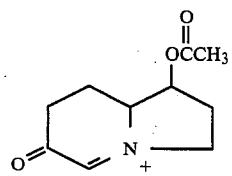

Depending upon the species in question and the state of the slaframine (i.e., whether as free base, salt or in other forms), the controlled dosage in accord with this invention can be administered orally, by injection or by inunction. However, regardless of the manner in which the slaframine dosage is administered, it should be purified (i.e., free of substantial quantities of swainsonine).

DESCRIPTION OF PREFERRED EMBODIMENTS

A variety of slaframine salts and derivatives can be used in accord with this invention. The preferred forms, however, include the carbamate, amide, dihydrochloride, dicitrate, and dipicrate salts. FIG. 2, below, illustrates the preferred carbamate derivative, while FIG. 3, below, illustrates the preferred amide derivative.

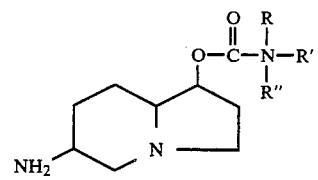

FIG. 2

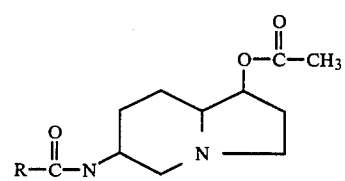

FIG. 3

The preferred dosage varies with the species. In young chickens, the preferred dosage range is between 0.25 and 1.00 milligrams of slaframine per kilogram, body weight, administered orally, once a day. In calves, the preferred dosage range is thought to be between 12 and 24 micrograms per kilogram, body weight, administered not more frequently than about once every 8–12 hours. In addition, those slaframine derivatives soluble in water can be administered via the drinking water.

The table set forth below summarizes the effects of slaframine on blood growth hormone concentration levels in a total of 69 chicks each of which was 21 days old.

| Hours After Administration | Treatment | | Significance |
|---|---|---|---|
| | Control[a] | Slaframine[b] | |
| | ng/ml[c] | | |
| 1 | 123 | 26 | .19 |
| 2 | 104 | 82 | .77 |
| 4 | 88 | 77 | .88 |
| 8 | 40 | 220 | .02 |
| 12 | 36 | 375 | .01 |

[a]Control = saline administered orally
[b]Slaframine (free base) orally administered at 1 mg/kg BW
[c]Nanograms blood growth hormone per milliliter blood plasma Although hormone levels appeared to decline in the 1–4 hour period following injection, the overall increase in hormone levels produced 8 to 12 hours after injection was dramatic. In one case, the concentration of hormone level increased by as much as 1000%.

That which is claimed is:

1. A method of promoting the release of growth hormones in an animal without causing debilitating side effects, said method comprising administering to said animal a controlled dosage of purified slaframine, its precursors, salts, derivatives or metabolites, said dosage being between 12 micrograms and 1 milligram per kilogram body weight.

2. The method of claim 1 wherein said derivative is the dihydrochloride, dicitrate, dipicrate, carbamate or amide of slaframine.

3. The method of claim 1 wherein said animal is a chick or other domesticated bird and said dosage is between 0.25 and 1.00 milligram per kilogram, body weight.

4. The method of claim 3 wherein said administering is effected orally.

5. The method of claim 1 wherein said animal is a cow, sheep or pig and said dosage is between 12 and 24 micrograms per kilogram, body weight.

6. The method of claim 5 wherein said derivative is the dihydrochloride, dicitrate, dipicrate, carbamate or amide of slaframine.

7. A method of promoting the release of growth hormones in an animal without causing debilitating side effects, said method comprising administering to said animal at least once each day a low level dosage of a chemical compound, which when activated in the body of said animal, forms 1-keto-6-aminooctahydroindolizine.

8. The method of claim 7 wherein said animal is a chick or other domesticated bird and said dosage is between 0.25–1.00 milligrams per kilogram, body weight, administered about once each day.

* * * * *